US008470407B2

(12) United States Patent
Badyal et al.

(10) Patent No.: US 8,470,407 B2
(45) Date of Patent: Jun. 25, 2013

(54) METHOD FOR PRODUCING A THIOL FUNCTIONALISED COATING

(75) Inventors: Jas Pal Singh Badyal, Wolsingham (GB); Wayne Christopher Schofield, Marlston-cum-Lache (GB)

(73) Assignee: Surface Innovations Ltd., Wolsingham, County Durham (GB)

( * ) Notice: Subject to any disclaimer, the term of this patent is extended or adjusted under 35 U.S.C. 154(b) by 945 days.

(21) Appl. No.: 11/918,415

(22) PCT Filed: Mar. 24, 2006

(86) PCT No.: PCT/GB2006/001051

§ 371 (c)(1), (2), (4) Date: Jun. 24, 2009

(87) PCT Pub. No.: WO2006/109014

PCT Pub. Date: Oct. 19, 2006

(65) Prior Publication Data

US 2009/0311555 A1 Dec. 17, 2009

(30) Foreign Application Priority Data

Apr. 15, 2005 (GB) ..................................... 0507612

(51) Int. Cl.
*C08F 2/46* (2006.01)
*C12Q 1/68* (2006.01)

(52) U.S. Cl.
USPC ........................................... 427/488; 435/6.1

(58) Field of Classification Search
USPC ........................................... 427/488; 435/6.1
See application file for complete search history.

(56) References Cited

U.S. PATENT DOCUMENTS

| | | | |
|---|---|---|---|
| 4,619,861 | A | 10/1986 | Nakayama et al. |
| 5,876,753 | A | 3/1999 | Timmons et al. |
| 6,306,506 | B1 | 10/2001 | Timmons et al. |

FOREIGN PATENT DOCUMENTS

| | | |
|---|---|---|
| WO | WO 97/38801 | 10/1997 |
| WO | WO 00/10012 | 2/2000 |

OTHER PUBLICATIONS

International Search Report for PCT/GB2006/001051, completed Jul. 10, 2006, mailed Aug. 3, 2006.

International Preliminary Report on Patentability for PCT/GB2006/001051, issued Oct. 16, 2007.

Written Opinion of the International Searching Authority for PCT/GB2006/001051, completed Jul. 10, 2006, mailed Aug. 3, 2006.

Communication in European Patent Application No. 06726473.9-2113, mailed Sep. 23, 2009.

*Primary Examiner* — Jezia Riley

(74) *Attorney, Agent, or Firm* — Clark & Elbing LLP

(57) ABSTRACT

A method is provided for applying a reactive thiol containing coating to a substrate. The method includes subjecting the substrate to a plasma discharge in the presence of a compound of formula (I) or formula (Ia): where X is an optionally substituted straight or branched alkylene chain(s) or aryl group(s); $R^1$, $R^2$ or $R^3$ are optionally substituted hydrocarbyl or heterocyclic groups, and m is an integer greater than 0; $R^n$ is a number of optionally substituted hydrocarbyl or heterocyclic groups, where n is 0-5.

(I)

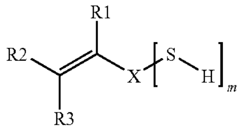

(Ia)

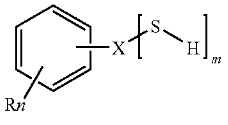

34 Claims, 7 Drawing Sheets

Scheme 1
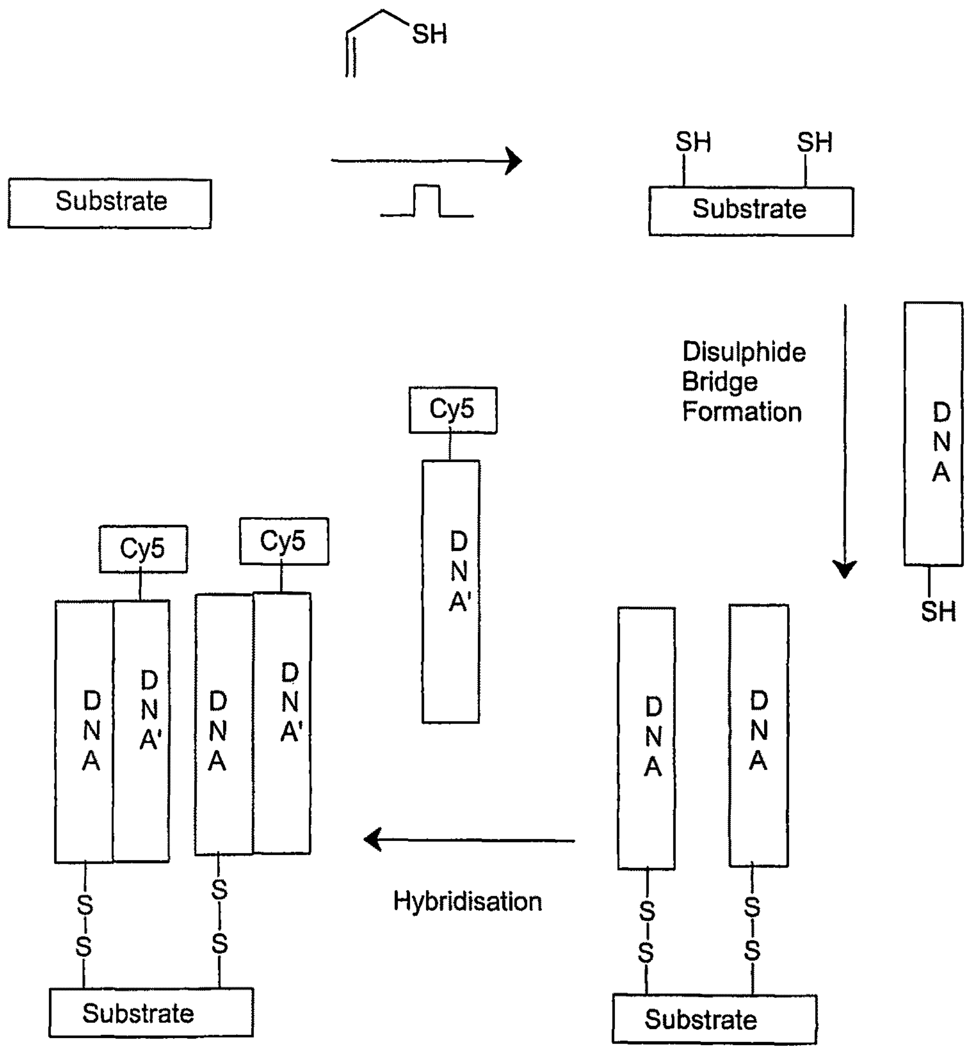

METHOD FOR PRODUCING A THIOL FUNCTIONALISED COATING

CROSS-REFERENCE TO RELATED APPLICATIONS

This application is the National Stage of International Application No. PCT/GB2006/001051 filed Mar. 24, 2006, which was published in English under PCT Article 21(2). This application also claims benefit of Great Britain Provisional Application No. 0507612.0, filed Apr. 15, 2005.

The present invention relates to the production of coatings which contain thiol functional groups.

The surface functionalisation of solid objects is a topic of considerable technological importance, since it offers a cost effective means of improving substrate performance without affecting the overall bulk properties. For instance, the attachment of biomolecules such as DNA or proteins is of great technical interest, allowing the construction of biological arrays that are finding application in fields of study as diverse as computing (Aldeman, M. *Science* 1994, 266, 1021; Frutos, A. G. et al., *Nuc. Acids Res.* 1997, 25, 4748), drug discovery (Debouck, C. et al., *Nature Genet.* 1999, 1(suppl.) 48), cancer research (Van't Veer, L. J. et al. *Nature* 2002, 415, 530) and the elucidation of the human genome (McGlennen, R. C. *Clinical Chemistry* 2001, 47, 393).

Furthermore, a thiol surface offers a chemically versatile substrate that allows surface modification by the application of widely used solution-based chemistries including, but not limited to, the Mannich reaction, the formation of disulphide bridges, nucleophilic addition, reaction with aldehydes, reaction with alkyl halides, reaction with ketones, reaction with noble and precious metals (such as gold and silver), the formation of sulphides and the oxidation or reduction of the thiol functionality.

Existing methods of attaching thiols to solid surfaces include mercapto-silane self-assembly (Levicky, R. et al, WO 2004113872), thiol self-assembly on gold using thiol groups on both ends of the linker molecule (Tivansky, A. V. et al *J. Phys. Chem. B.* 2005, 109, 5398), and the Immobilisation of thiol containing linkers to other functionalised surfaces (Stechen, M. et al., Electrochemistry Communications 2005, 7, 416; Lucarelli et al., Biosensors and Bioelectronics 2005, 20, 2001). All of these approaches suffer from drawbacks including involving multi-step processes, substrate specificity, and the requirement for solution phase chemistry.

Another method of forming thiol functionality on a surface comprises the treatment of a polymer surface, such as polyethylene, with a sulphur containing gas plasma, such as hydrogen sulphide. However, such approaches lead to the generation of a wide range of surface functional groups such as sulphides and episulphides (Muguruma, H. et al., *Chemistry Letters* 1996, 4, 283).

Surface functionalisation by continuous wave plasma polymerisation is an additional route by which thiols have been attached to solid surfaces. This approach suffers from the drawback of poor structural retention, with surfaces showing increased sulphonation and/or a loss of thiol functionality compared to their monomer precursors (Roh, J. H. et al. *Journal of Adhesion Science and Technology,* 2002, 16, 1529; Thyen, R. et al. PCT Int. Appl. WO 2001076773).

Plasma polymers are hence often regarded as being structurally dissimilar compared to conventional polymers, since they possess high levels of cross-linking and lack a regular repeat unit (Yasuda, H. *Plasma Polymerisation* Academic Press: New York, 1985). This can be attributed to the plasma environment generating a whole range of reactive intermediates that contribute to an overall lack of chemical selectivity. However, it has been found that pulsing the electric discharge on the ms-μs timescale can significantly improve structural retention of the parent monomer species (Panchalingam, V. et al., *Appl. Polym, Sci,* 1994, 54, 123; Han, L. M. et al., *Chem. Mater.,* 1998, 10, 1422; Timmons et al., U.S. Pat. No. 5,876,753) and in some cases conventional linear polymers have been synthesised (Han, L. M. et al., *J. Polym. Sci., Part A: Polym. Chem.* 1998, 36, 3121). Under such conditions, repetitive short bursts of plasma are understood to control the number and lifetime of active species created during the on-period, which then is followed by conventional reaction pathways (e.g. polymerisation) occurring during the off-period (Ryan, M. E. et al., *Chem. Mater.,* 1996, 8, 37).

The preparation of thiol functionalised surfaces by continuous-wave plasma polymerisation has been previously reported using ethanethiol (Maguruma, H. et al. *Chemistry Letters* 1996, 4, 283). However, the retention of monomer structure was poor and the coated surfaces exhibited low levels of usable thiol functionality. The observed inadequate level of sample performance was largely due to the structure of the monomer utilised. Ethanethiol lacks a functional group, such as an acrylate or alkene functionality, that can be readily polymerised by conventional reaction pathways during the pulsed plasma off-time. Hence, in order for deposition to occur from such monomers, relatively harsh plasma conditions must be applied, sufficient to initiate polymerisation via normally non-polymerisable functional groups (e.g. alkyl moieties). Clearly conditions capable of rupturing and reattaching such unsaturated structures to one another are equally capable of destroying the desired thiol functionality. This inevitably leads to the poor degree of monomer retention observed in previous experiments. To achieve the successful deposition of a thiol containing surface, a methodology combining both pulsed plasma techniques and the selection of a suitable polymerisable monomer structure must be utilised.

The applicants have found that pulsed plasma polymerisation of monomers containing thiol functionalities of general formula (I) or formula (Ia) can potentially overcome the limitations of existing techniques for forming thiol functionalised surfaces. Compounds of formula (I) or formula (Ia) possess unsaturated functional groups (such as alkene, acrylate, methacrylate and phenyl) that can undergo conventional polymerisation pathways during the pulsed plasma off-time with negligible impact on the desired thiol moiety. The resulting films, in comparison with the prior art, exhibit almost total retention of monomer functionality and have been found capable of the exacting levels of performance demanded by applications such as DNA microarray production.

According to the present Invention there is provided a method for applying a reactive thiol containing coating to a substrate, said method including subjecting said substrate to a plasma discharge in the presence of a compound of formula (I) or formula (Ia):

(I)

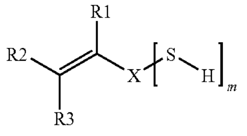

-continued (Ia)

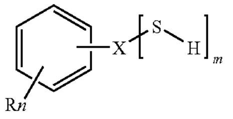

Where X is an optionally substituted straight or branched alkylene chain(s) or aryl group(s); $R^1$, $R^2$, or $R^3$ are optionally substituted hydrocarbyl or heterocyclic groups; $R''$ is a number of optionally substituted hydrocarbyl or heterocyclic groups, where n may take values from 0 to 5; and m is an integer greater than 0.

As used herein, the term "hydrocarbyl" includes alkyl, alkenyl, alkynyl, aryl and aralkyl groups. The term "aryl" refers to aromatic cyclic groups such as phenyl or naphthyl, in particular phenyl. The term "alkyl" refers to straight or branched chains of carbon atoms, suitably of from 1 to 20 carbon atoms in length. The terms "alkenyl" and "alkynyl" refer to straight or branched unsaturated chains suitably having from 2 to 20 carbon atoms. These groups may have one or more multiple bonds. Thus examples of alkenyl groups include allenyl and dienyl.

Suitable optional substituents for hydrocarbyl groups $R^1$, $R^2$, $R^3$ and alkylene/aryl groups X are groups that are substantially inert during the process of the invention. They may include halo groups such as fluoro, chloro, bromo and/or iodo. Particularly preferred halo substituents are fluoro.

In a preferred embodiment of the invention, X is a moiety comprising an ester group adjacent to an optionally substituted hydrocarbyl or heterocyclic group, $R^4$. Thus, in a particular embodiment, the compound of formula (I) is a compound of formula (II):

(II)

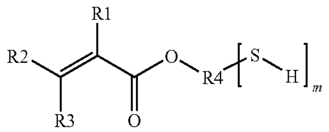

In particular, $R^1$, $R^2$, $R^3$ and $R^4$ are independently selected from hydrogen or alkyl, and in particular, from hydrogen or $C_{1-6}$ alkyl, such as methyl. Thus, in a particularly preferred embodiment, the compound of formula (II) is a compound of formula (III): the desired thiol functionality is connected to a readily polymerised acrylate group ($CH_2{=}CH{-}CO_2{-}$) via a saturated alkyl hydrocarbon chain linker, $R^4$, where n is an integer of from 1 to 20:

(III)

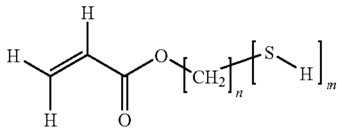

A particular example of a compound of formula (III), where m=1 and n=1, is 2-mercaptoethyl acrylate.

In another particularly preferred embodiment, the compound of formula (II) is a compound of formula (IIIa): the desired thiol functionality is connected to a readily polymerised methacrylate group ($CH_2{=}C(CH_3){-}CO_2{-}$) via a saturated alkyl hydrocarbon chain linker, $R^4$, where n is an integer of from 1 to 20:

(IIIa)

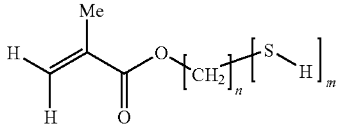

A particular example of a compound of formula (IIIa), where m=1 and where n=1, is 2-mercaptoethyl methacrylate In other particularly preferred embodiments of the invention, with reference to the compound of formula (I), $R^1$, $R^2$ and $R^3$ are again independently selected from hydrogen or alkyl, and in particular, from hydrogen or $C_{1-6}$ alkyl, such as methyl. Thus, in another particular embodiment, the compound of formula (I) is a compound of formula (IV):

(IV)

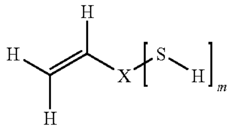

where X is as defined above and m is an integer greater than 0.

Particularly preferred compounds of formula (IV) are vinylbenzenes of formula (V), where X is a di-substituted aromatic ring:

(V)

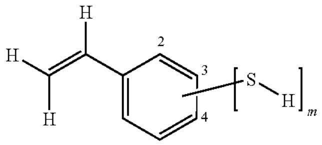

where the ring can be ortho, meta or para substituted.

A particular example of a compound of formula (V) is 4-mercaptostyrene.

In another particularly preferred example of the compound of formula (IV), X is a saturated alkyl hydrocarbon chain. Thus, the compound of formula (IV) is a compound of formula (V) where n is an integer of from 1 to 20, for example from 1 to 10 and preferably 8.

(Va)

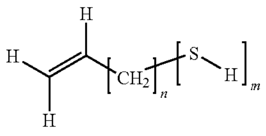

A particular example of a compound of formula (Va), where m=1 and n=1, is allyl mercaptan.

Precise conditions under which the pulsed plasma deposition of the compound of formula (I) takes place in an effective manner will vary depending upon factors such as the nature of the monomer, the substrate, the size and architecture of the plasma deposition chamber etc. and will be determined using routine methods and/or the techniques illustrated hereinafter. In general however, polymerisation is suitably effected using vapours or atomised droplets of compounds of formula (I) at pressures of from 0.01 to 999 mbar, suitably at about 0.2 mbar. Although atmospheric-pressure and sub-atmospheric pressure plasmas are known and utilised for plasma polymer deposition in the art.

A glow discharge is then ignited by applying a high frequency voltage, for example at 13.56 MHz. The applied fields are suitably of an average power of up to 50 W.

The fields are suitably applied for a period sufficient to give the desired coating. In general, this will be from 30 seconds to 60 minutes, preferably from 1 to 15 minutes, depending upon the nature of the compound of formula (I) and the substrate etc.

Suitably, the average power of the pulsed plasma discharge is low, for example of less than 0.05 $W/cm^3$, preferably less than 0.025 $W/cm^3$ and most preferably less than 0.0025 $W/cm^3$.

The pulsing regime which will deliver such low average power discharges will vary depending upon the nature of the substrate, the size and nature of the discharge chamber etc. However, suitable pulsing arrangements can be determined by routine methods in any particular case. A typical sequence is one in which the power is on for from 1 μs to 100 μs, and off for from 100 μs to 20000 μs.

In one embodiment of the invention the pulsing regime is varied during the course of coating deposition so as to enable the production of gradated coatings. For example, a high average-power pulsing regime may be used at the start of sample treatment to yield a highly cross-linked, insoluble sub-surface coating that adheres well to the substrate. A low average-power pulsing regime may then be adopted for conclusion of the treatment cycle, yielding a surface layer displaying high levels of retained monomer thiol functionality on top of said well-adhered sub-surface. Such a regime would be expected to improve overall coating durability and adhesion, without sacrificing any of the desired surface properties (i.e. reactive surface thiol functionality).

Suitable plasmas for use in the method of the invention include non-equilibrium plasmas such as those generated by audio-frequencies, radiofrequencies (RF) or microwave frequencies. In another embodiment the plasma is generated by a hollow cathode device. In yet another embodiment, the pulsed plasma is produced by direct current (DC).

The plasma may operate at low, sub-atmospheric or atmospheric pressures as are known in the art. The monomer may be introduced into the plasma as a vapour or an atomised spray of liquid droplets (WO03101621 and WO03097245, Surface Innovations Limited). The monomer may be introduced into the pulsed plasma deposition apparatus continuously or in a pulsed manner by way of, for example, a gas pulsing valve The substrate to which the thiol bearing coating is applied will preferentially be located substantially inside the pulsed plasma during coating deposition, However, the substrate may alternatively be located outside of the pulsed plasma, thus avoiding excessive damage to the substrate or growing coating.

The monomer will typically be directly excited within the plasma discharge. However, "remote" plasma deposition methods may be used as are known in the art. In said methods the monomer enters the deposition apparatus substantially "downstream" of the pulsed plasma, thus reducing the potentially harmful effects of bombardment by short-lived, high-energy species such as ions.

The plasma may comprise the monomeric compound alone, in the absence of other compounds or in admixture with for example an inert gas. Plasmas consisting of monomeric compound alone may be achieved as illustrated hereinafter, by first evacuating the reactor vessel as far as possible, and then purging the reactor vessel with the organic compound for a period sufficient to ensure that the vessel is substantially free of other gases. The temperature in the plasma chamber is suitably high enough to allow sufficient monomer in gaseous phase to enter the plasma chamber. This will depend upon the monomer and conveniently ambient temperature will be employed. However, elevated temperatures for example from 25 to 250° C. may be required in some cases.

In alternative embodiments of the invention, materials additional to the plasma polymer coating precursor are present within the plasma deposition apparatus. The additional materials may be introduced into the coating deposition apparatus continuously or in a pulsed manner by way of, for example, a gas pulsing valve.

Said additive materials may be inert and act as buffers without any of their atomic structure being incorporated into the growing plasma polymer (suitable examples include the noble gases). A buffer of this type may be necessary to maintain a required process pressure. Alternatively the inert buffer may be required to sustain the plasma discharge. For example, the operation of atmospheric pressure glow discharge (APGD) plasmas often requires large quantities of helium. This helium diluent maintains the plasma by means of a Penning Ionisation mechanism without becoming incorporated within the deposited coating.

In other embodiments of the invention, the additive materials possess the capability to modify and/or be incorporated into the coating forming material and/or the resultant plasma deposited coating. Suitable examples include other reactive gases such as halogens, oxygen, and ammonia.

In alternative embodiments of the invention, the additive materials may be other monomers. The resultant coatings comprise copolymers as are known and described in the art. Suitable monomers for use within the method of the invention include organic (e.g. styrene), inorganic, organo-silicon and organo-metallic monomers.

The invention further provides a substrate having a thiol containing coating thereon, obtained by a process as described above. Such substrate can include any solid, particulate, or porous substrate or finished article, consisting of any materials (or combination of materials) as are known in the art. Examples of materials Include any or any combination of, but are not limited to, woven or non-woven fibres, natural fibres, synthetic fibres, metal, glass, ceramics, semiconductors, cellulosic materials, paper, wood, or polymers such as polytetrafluoroethylene, polythene or polystyrene. In a particular embodiment, the surface comprises a support material, such as a polymeric material, used in biochemical analysis.

In one embodiment of the invention the substrate is coated by means of a reel-to-reel apparatus. This process can be continuous. In one embodiment the substrate is moved past and through a coating apparatus acting in accordance with this invention.

The pulsed plasma polymerisation of the invention is therefore a solventless method for functionalising solid surfaces with thiol groups.

The method of the invention may result in a product wholly coated In a thiol functionalised polymer coating.

In an alternative aspect of the invention the thiol functionalised polymer coating Is only applied to selected surface domains.

The restriction of the thiol functionalised polymer coating to specific surface domains may be achieved by limiting the means of coating production of the method to said specific surface domains. In one embodiment of this aspect of the invention, the aforementioned spatial restriction is achieved by plasma depositing the thiol functionalised coating through a mask or template. This produces a sample exhibiting regions covered with thiol functionalised polymer juxtaposed with regions that exhibit no thiol functionality.

An alternative means of restricting thiol functionalization to specific surface domains includes: depositing the thiol functionalised polymer over the entire surface of the sample or article, before rendering selected areas of it non-thiol functionalised. This spatially selective removal/damage of the thiol functionalised polymer may be achieved using numerous means as are described in the art. Suitable methods include, but are not limited to, electron beam etching and exposure to ultraviolet irradiation through a mask. The pattern of non-transmitting material possessed by the mask is hence transferred to areas of thiol functionalisation.

Once the thiol functional coating has been applied to the substrate, the thiol group may be further derivatised as required. In particular, it may be reacted with another thiol, such as a thiol terminated oligonucleotide strand, to form a disulphide bridge linkage. The derivatisation reaction may be effected in the gaseous phase where the reagents allow, or in a solvent such as water or an organic solvent. Examples of such solvents include alcohols (such as methanol), and tetrahydrofuran.

The derivatisation may result in the immobilisation of thiol containing reagent on said surface. If derivatisation is spatially addressed, as is known in the art, this results in chemical patterning of the surface. A preferred case of a thiol surface patterned with thiol containing biomolecules is a biological microarray. A particularly preferred case is one in which the thiol containing biomolecule is a DNA strand, resulting in a DNA microarray. Another preferred embodiment is one in which the thiol containing biomolecule is a protein or fragment thereof, resulting in a protein microarray.

Thiol functionalised surfaces produced In accordance with the invention were derivatized with a variety of thiol-containing reagents (e.g. derivatized oligonucleotide strands, proteins, and sugars). Furthermore, these thiol functionalised surfaces produced in accordance with the invention enabled the construction of DNA microarrays by a procedure shown diagrammatically in Scheme 1.

Thus in a further embodiment, the invention provides a method for the immobilisation of a thiol containing reagent at a surface, said method including the application of a reactive thiol containing coating to said surface by a plasma deposition method described above, and then contacting the coating surface with a solution of said thiol-containing reagent under conditions such that the thiol-containing agent reacts with the surface thiol groups.

A further embodiment includes said method of derivitizing a thiol containing coating with a thiol containing reagent using the method described above, and then stripping said attached thiol-containing reagent under conditions such that the thiol-containing reagent is reversibly removed from the thiol containing coating. Further the thiol containing coating produced in this invention could be rederivitized with thiol containing agents several times, creating a re-writable surface.

In an additional embodiment of the method, the thiol containing coatings produced in accordance with the invention may be derivatized with reagents containing noble or precious metals. Said reagents may be particulate in nature, examples include, but are not restricted to colloidal solutions of gold or silver nano-particles.

Pulsed plasma polymerization in accordance with the invention has been found to be an effective means for functionalizing solid substrates with thiol groups. The resulting functionalised surfaces are amenable to conventional thiol derivatization chemistries.

The invention will now be particularly described by way of examples with reference to the accompanying drawings in which.

Figure 5:
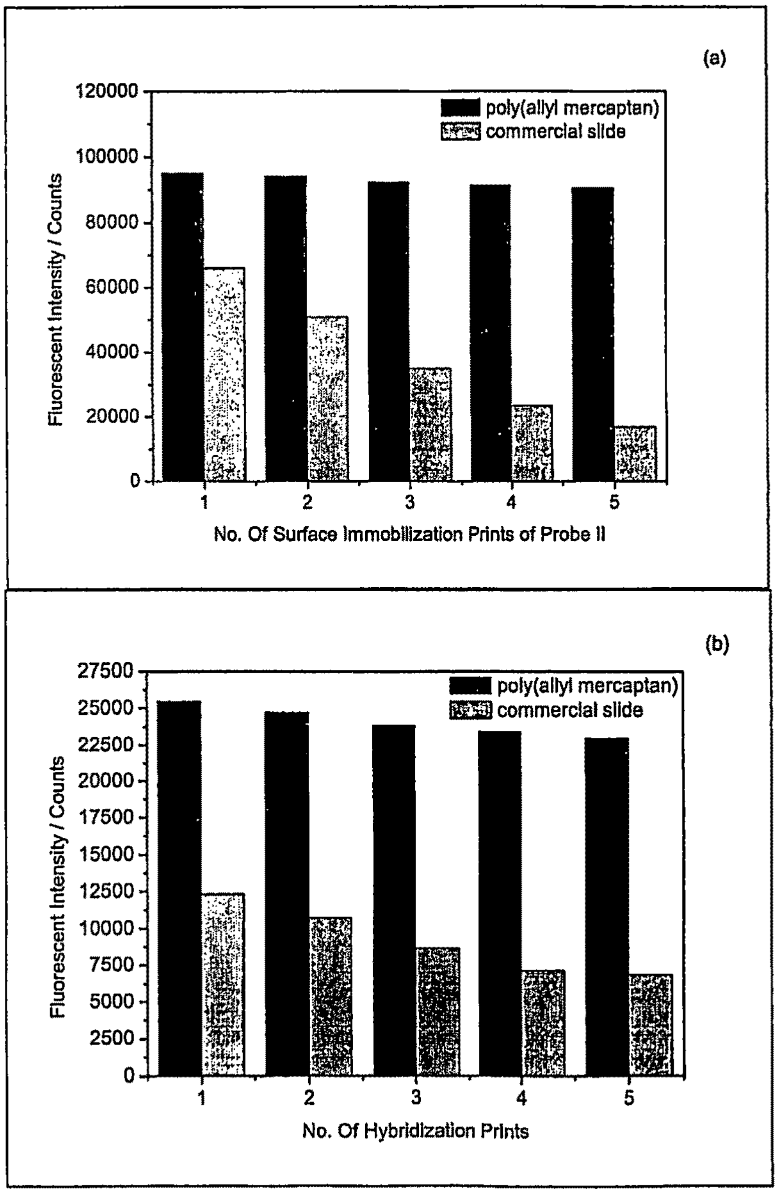

FIG. 5 demonstrates the fluorescent intensity at the surface of allyl mercaptan pulsed plasma polymer layers: (a) after stripping and re-immobilization of DNA oligonucleotide Probe II; and (b) after the removal of hybridised DNA oligonucleotide Probe III from surface-bound DNA oligonucleotide Probe I and subsequent re-exposure to a solution of Probe III. Where the plasma coating is poly(allyl mercaptan) and the thiol coated commercial slide was supplied by CEL Associates, Inc. (Pearland, Tex.).

Figure 6:
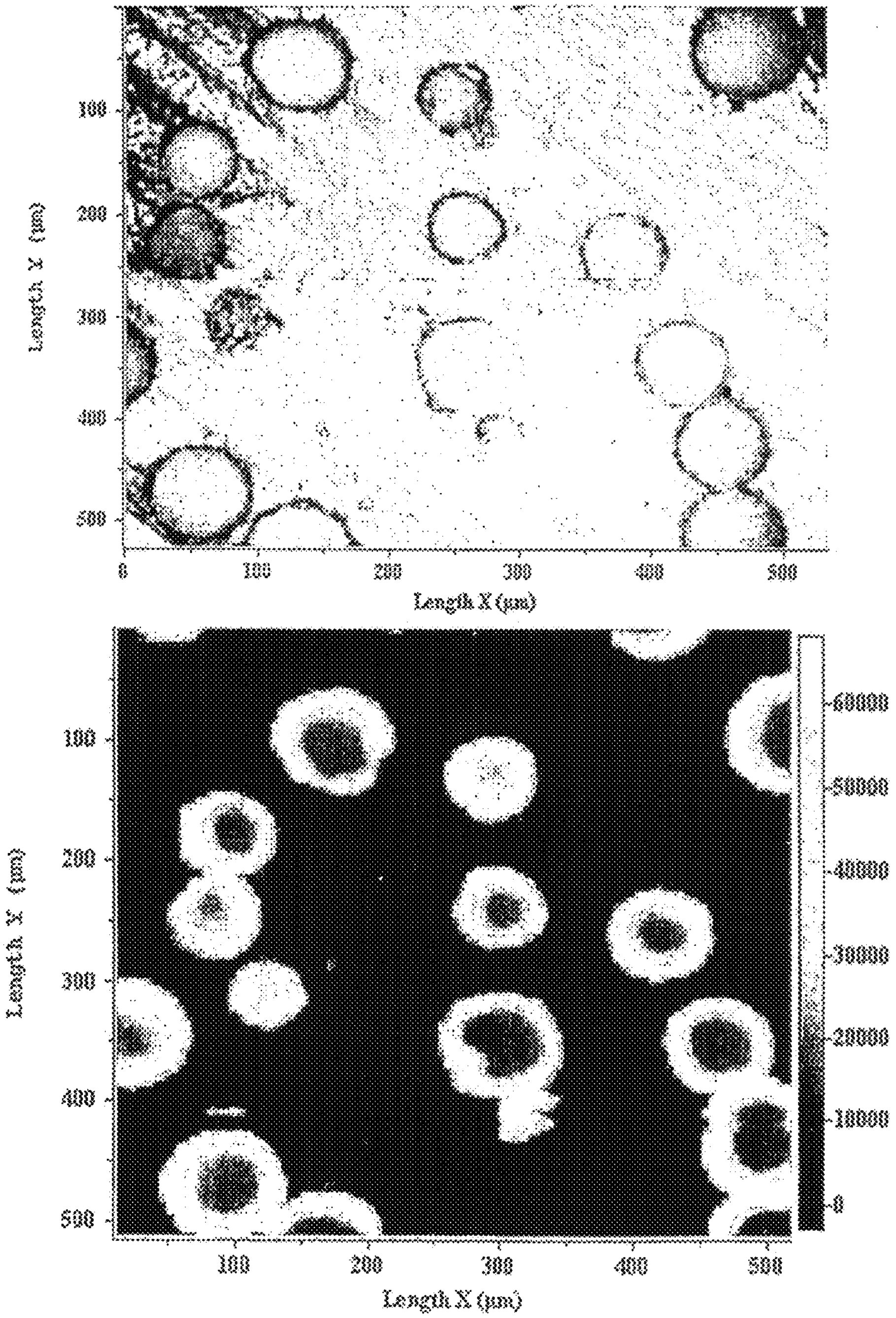

FIG. 6 shows Cy5 tagged ssDNA probe II immobilised onto allyl mercaptan functionalised treated polystyrene beads. Examined by (a) visible microscopy, and (b) fluorescence microscopy.

Scheme 1 shows a method of the invention for enabling DNA hybridisation on surfaces: (a) Thiol surface functionalisation by pulsed plasma polymerisation of allyl mercaptan, (b) Immobilisation of thiol terminated ssDNA onto the pulsed plasma polymer surface by disulphide bridge formation chemistry, and (c) Hybridisation of complementary Cy5 tagged ss DNA to surface immobilised ssDNA.

The following examples are intended to illustrate the present invention but are not intended to limit the same:

EXAMPLE 1

Plasma polymerization of allyl mercaptan (Aldrich, 80%, $H_2C{=}CH(CH_2)SH$, purified by several freeze-pump thaw cycles) was carried out in an electrodeless cylindrical glass reactor (5 cm diameter, 520 $cm^3$ volume base pressure $3\times10^{-2}$ mbar, leak rate=$1\times10^{-9}$ mol $s^{-1}$) enclosed in a Faraday Cage. The chamber was fitted with a gas inlet, a thermocouple pressure gauge and a 30 L $min^{-1}$ two-stage rotary pump connected to a liquid nitrogen cold trap. All joints were grease free. An externally wound 4 mm diameter copper coil spanned 8-15 cm from the gas inlet with 9 turns.

The output impedance of a 13.56 MHz RF power supply was matched to the partially ionized gas load with an L-C matching network. In the case of pulsed plasma deposition, the RF source was triggered from an external signal generator, and the pulse shape monitored with a cathode ray oscilloscope. The reactor was cleaned by scrubbing with detergent, rinsing in water, propan-2-ol and drying in an oven. The reactor was further cleaned with a 0.2 mbar air plasma operating at 40 W for a period of 30 min. Each substrate was sonically cleaned in a 50:50 mixture of cyclohexane and propan-2-ol for 10 min and then placed into the centre of the reactor on a flat glass plate.

Figure 1:
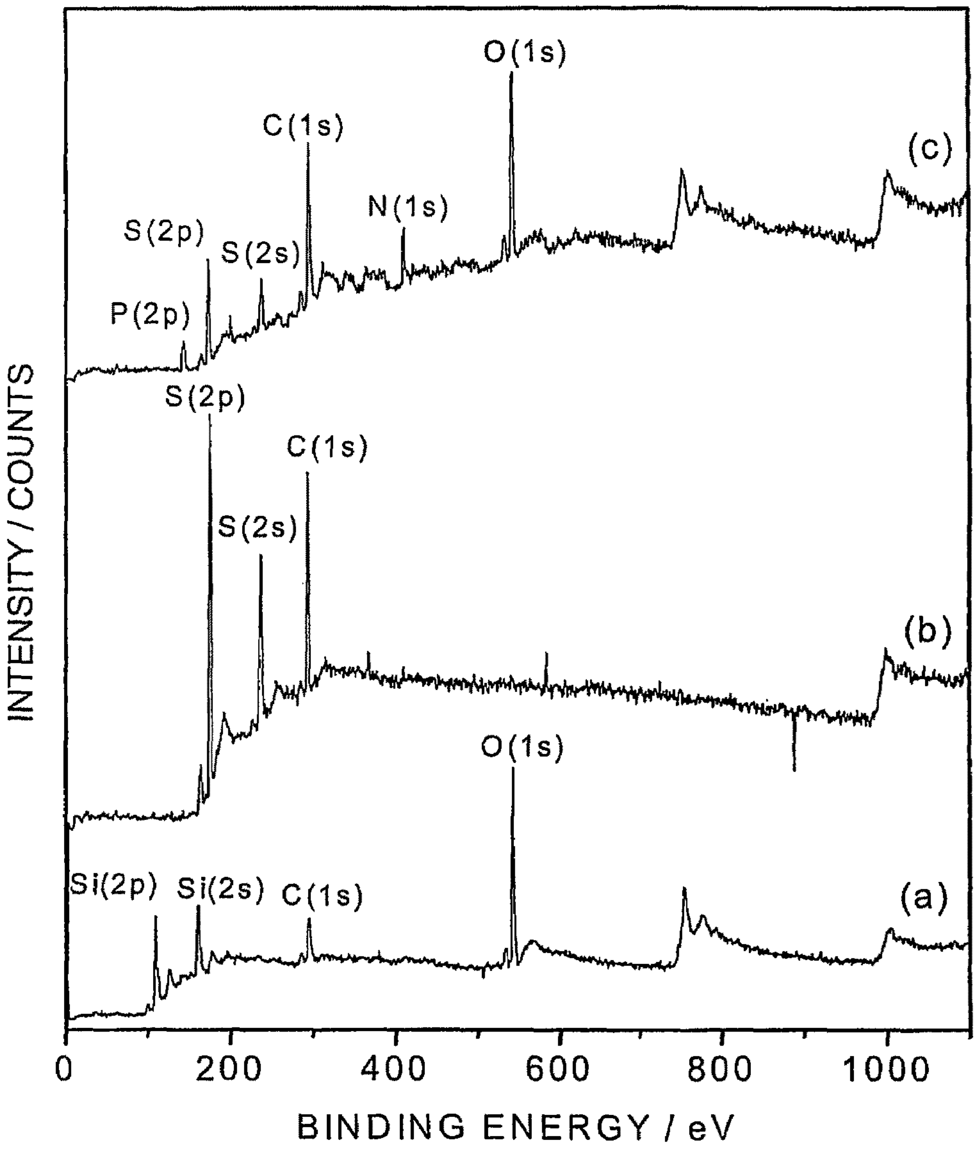
FIG. 1 shows the XPS spectra of (a) a silicon wafer, (b) an allyl mercaptan pulsed plasma polymer layer ($P_p$=40 W; $t_{on}$=100 μs; $t_{off}$=4 ms; deposition time=10 min), and (c) a DNA oligonucleotide (Probe I) deposited from 200 nM solution onto the allyl mercaptan pulsed plasma polymer surface.

XPS analysis of the plasma poly(allyl mercaptan) layers confirmed the presence of only carbon and sulphur; the surface, with no Si(2p) signal from the underlying silicon substrate showing through, FIG. 1 and Table 1. The corresponding S(2p) peak for the pulsed plasma polymer film occurred at a binding energy of 163 eV, indicating a thiol as the major sulphur species present (Moulder, J. F.; Stickle, W. F.; Sobol, P. E Bomben, K. D. *Handbook of X-ray Photoelectron Spectroscopy*, Perkin Elmer Corporation: Eden Prairie, Mich. 1992; Terasaki, N.; Akiyama, T.; Yamada, N. *Langmuir* 2002, 18, 8666).

TABLE 1

XPS Atomic Percentage for pulsed plasma deposited allyl mercaptan layers

| Surface | Elemental Abundance % C | % N | % O | % P | % S |
|---|---|---|---|---|---|
| Allyl mercaptan, pulsed plasma polymer. | 76 ± 1 | 0 | 0 | 0 | 24 ± 1 |
| Allyl mercaptan, theoretical | 75 | 0 | 0 | 0 | 25 |
| Oligonucleotide Probe I, on allyl mercaptan plasma polymer | 46 ± 1 | 10 ± 1 | 24 ± 1 | 4 ± 1 | 16 ± 1 |
| Oligonucleotide Probe I, theoretical | 49 | 13 | 32 | 5 | <1 |

Figure 2:
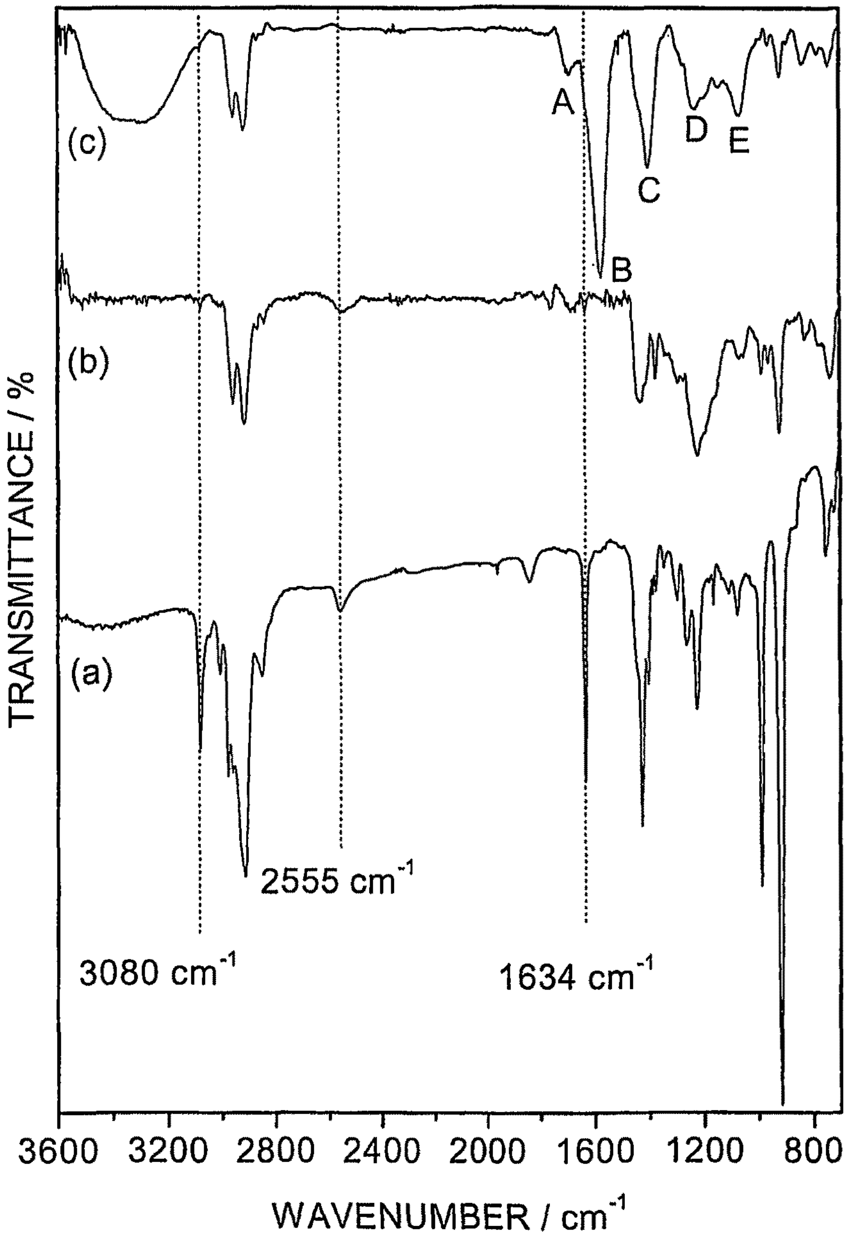
FIG. 2 shows the Infrared spectra of (a) the allyl mercaptan monomer, (b) the allyl mercaptan pulsed plasma polymer layer ($P_p$=40 W; $t_{on}$=100 μs; $t_{off}$=4 ms; deposition time=10 min), and (c) a DNA oligonucleotide (Probe I) deposited from 200 nM solution onto (b).

Infrared spectroscopy was used to evaluate the molecular structure of the pulsed plasma poly(allyl mercaptan) films and the subsequently immobilised oligonucleotides, FIG. 2. For the allyl mercaptan monomer, the following band assignments were made: allyl C—H stretch (3080 $cm^{-1}$); allyl $CH_2$ stretch (3031 $cm^{-1}$); alkyl $CH_2$ stretch (2891 $cm^{-1}$); thiol S—H stretch (2555 $cm^{-1}$); allyl C═C stretch (1634 $cm^{-1}$) (Lin-Vien, D. et al. *The Handbook of Infrared and Raman Characteristic Frequencies of Organic Molecules*; Academic Press: New York, 1991). All of the bands associated with the allyl mercaptan monomer were clearly discernible following pulsed plasma polymerisation, except for the allyl carbon-carbon double bond features that had disappeared during polymerisation. The continued presence of the infrared band belonging to the thiol feature confirmed that structural retention of the thiol group had occurred during electrical pulsing conditions.

EXAMPLE 2

DNA immobilization to pulsed plasma polymerised allyl mercaptan surfaces entailed immersing oligonucleotide Probe I (Table 2) into a sodium chloride/sodium citrate buffer (3 M NaCl, 0.3 M Na Citrate—$2H_2O$, pH 4.5, Aldrich) to final concentration of between 50 nM to 400 nM was immobilised onto the pulsed plasma polymer film. The oligonucleotide buffered solution was placed onto freshly prepared pulsed plasma poly(allyl mercaptan) surfaces using a pipette tip. The surfaces were subsequently incubated for 16 hours at room temperature in a humidified chamber (64% relative humidity) to prevent the spots from drying (when drops dry solutes are transported to their rims, leading to an uneven concentration distribution) and then washed three times using water and buffer solution. The spotted surfaces were then dried with nitrogen gas to ensure that they were solvent and dust free.

TABLE 2

Oligonucletide sequences used in the study (synthesized by Sigma-Genosys Ltd).

| Oligo-nucleotide Label | Base Sequence (5' to 3') | | Fluorophore | Linker |
|---|---|---|---|---|
| Probe I | GCTTATCGAGCTTTC | (SEQ ID NO. 1) | N/A | 5'-HS-$(CH_2)_6$- |
| Probe II | GCTTATCGAGCTTTC | (SEQ ID NO. 2) | 3'-[CY5]- | 5'-HS-$(CH_2)_6$- |
| Probe III | GAAAGCTCGATAAGC | (SEQ ID NO. 3) | 5'-[CY5]- | N/A |
| Probe IV | CGAATAGCTCGAAAG | (SEQ ID NO. 4) | N/A | 5'-HS-$(CH_2)_6$- |

XPS analysis of pulsed plasma poly(allyl mercaptan) layers exposed to oligonucleotide Probe I indicated the presence of several elements including carbon, nitrogen, oxygen, sulphur (as sulphide or disulphide centres, Binding Energy: 161.4 eV) and phosphorous centres, FIG. 1 and Table 1. No evidence of sodium or chlorine from the buffer solutions was detected. A binding energy shift of the S(2p) peak was attributed to successful oligonucleotide Probe I immobilisation to the surface, Scheme 1. However, intra-polymer and inter-polymer disulphide bridge formation within the pulsed plasma poly(allyl mercaptan) layer could also have contributed to this disulphide peak.

Figure 3:
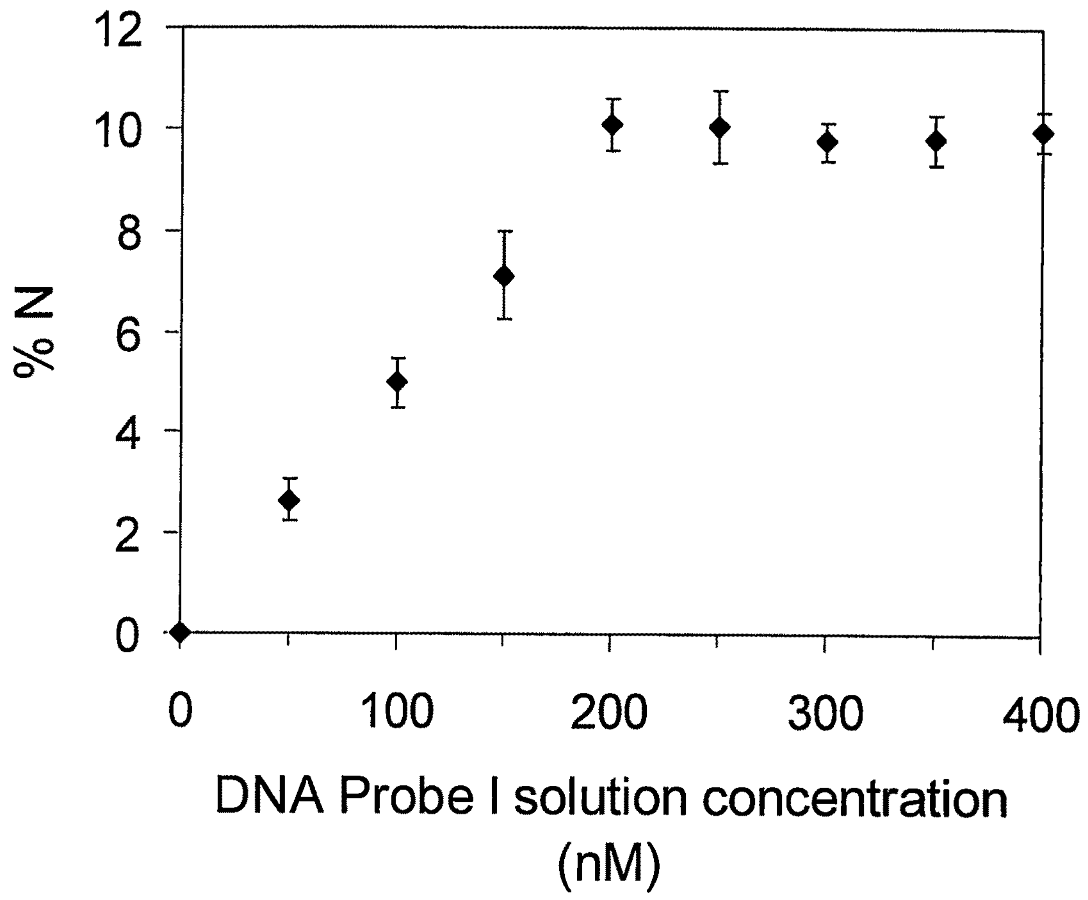
FIG. 3 is a graph showing the variation in atomic nitrogen concentration (% N) at the surface of the pulsed plasma poly(allyl mercaptan) layer following DNA Probe I immobilisation as a function of solution concentration.

The corresponding rise in the intensity of the N(1s) peak at ~400 eV also indicated ssDNA attachment to the pulsed plasma pol(allyl mercaptan) surface. The packing density of ssDNA at the surface could be varied by diluting the solution with buffer, FIG. 3. For the ssDNA probe I oligonucleotide under investigation, the surface concentration of nitrogen (% N) was found to correlate to the degree of dilution. Surface saturation levels corresponded to dilutions above 150 nM.

EXAMPLE 3 ssDNA microarrays were generated on fresh poly(allyl mercaptan) pulsed plasma layers using a robotic microarrayer (Genetix Inc) equipped with micro-machined pins that consistently delivered samples of ~1 mL (200 nM buffered ssDNA solution) onto the pulsed plasma poly(allyl mercaptan) coated glass slides (18×18×0.17 mm, BDH) at designated locations. Circular spots with diameters ranging from 100-125 μm and with a minimum print pitch of 110 μm could be routinely obtained. After spotting, the DNA oligonucleotide immobilised slides were kept in a humidity chamber (64% relative humidity) for 24 hours at 60° C. Finally, the slides were removed and washed with buffer solution and copious amounts of water. Probe I, II and IV were used in the spotting process.

ssDNA microarrays and fully immobilised surfaces of Probe I and IV were subsequently exposed to a hybridisation solution of Probe III in hybridisation buffer (consisting of 6×SSC pH 7, 5×Denhardt's solution (1% BSA (bovine serum albumin), 2% Ficoll 400, and 2% polyvinylpyrollidone (PVP)), 0.5% sodium dodecyl sulphate (SDS), and sheared salmon sperm DNA (55 ug/mL) to a final concentrations of 400 nM. Two small strips of adhesive tape were affixed along the rim of the ssDNA oligonucleotide functionalised Probe I and IV slides and then covered with a cleaned microscope slide cover glass. The cavity formed between the chip and the cover glass was then slowly filled with 10 μL of the hybridisation solution by capillary force. This slide was then incubated in a humidified hybridisation chamber (100 μL of water was placed next to the chip) immersed in a 55° C. water bath for 2 hours. After the cover glass was removed, the chip was washed three times with buffer solution and then with copious amounts of water and blow dried with nitrogen gas. The stripping of the bound oligonucleotides of the chip were investigated placing into a boiling solution of (a) 200 nM TrisCl pH 7.0, 0.1×SSC and 0.1% (w/v) SDS for 10 mins or (b) 0.1% (w/v) SDS for 10 mins in order to remove the labelled oligonucleotides.

Fluorescent microscopy was used to assess the viability of producing microarrays using allyl mercaptan pulsed plasma polymer layers as a substrate. Fluorescence mapping of resultant arrays was achieved using a Dilor Labram microscope utilizing a 20 mW He:Ne laser with a wavelength of 632.817 nm (corresponds to the excitation frequency of the Cy5 fluorophore) and a polarization of 500:1, which was passed through a diffraction grating of 1800 lines $mm^{-1}$. In the case of the immobilisation of oligonucleotide Probe II, a fluorescent image of an array of spots with an average diameter of 125 microns and a print pitch of 150 microns was obtained in accordance with the spotting parameters used, FIG. 4*a*. In the case of the hybridised arrays, a similar pattern was obtained on the surface, however, the spot size had increased to 150 microns in diameter and the spots had an inhomogeneous outer edge density signal, FIG. 5*b*.

Figure 4:
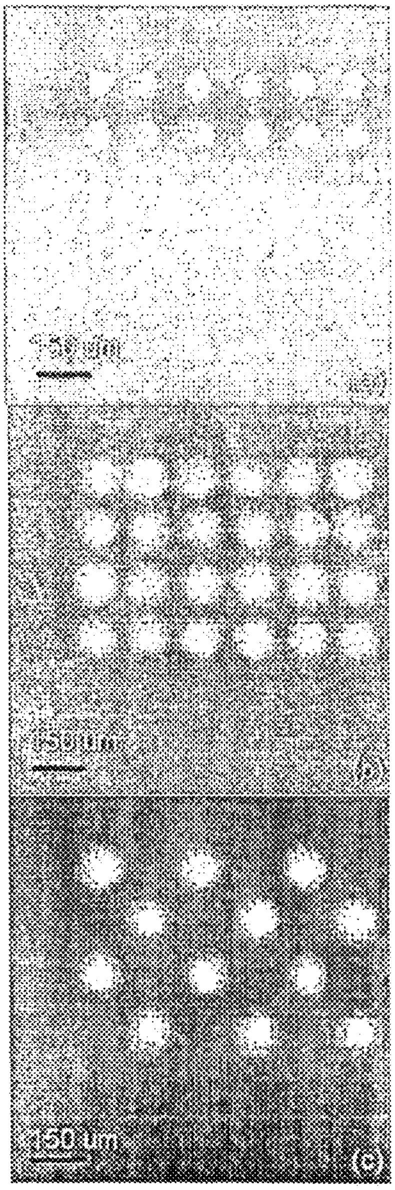
FIG. 4 shows fluorescent microscope images of DNA micro-spotted arrays produced on allyl mercaptan pulsed plasma polymer layers: (a) oligonucleotide Probe II; (b) oligonucleotide Probe II subsequently hybridized with oligonucleotide probe III; and (c) oligonucleotide Probe I and IV in alternating pattern and subsequently hybridized with oligonucleotide Probe III.

No measurable non-specific hybridisation signal from the non-complementary control oligonucleotide (Probe IV) was detected, FIG. 4*c*. It was also observed that less than 5% of the disulphide bound oligonucleotides were detached from the solid support when treated with hybridization salts used in this example for 48 hours at room temperature.

EXAMPLE 4

The comparative reusability of the allyl mercaptan chips prepared in Example 2, and commercial thiol-coate glass chips (CEL Associates, Pearland, Tex.) was investigated by stripping the bound oligonucleotides froi the chips by placing into a boiling solution of (a) 200 nM TrisCl pH 7.0, 0.1×SSC and 0.1% (w/v) SDS for 1 mins or (b) 0.1% (w/v) SDS for 10 mins.

Both types of chips were Investigated by stripping; using high-stringency washes and low-stringency washes to remove immobilized and hybridized oligonucleotides from the surface respectively. After the first instance of the removal of the immobilized oligonucleotides followed by another set of immobilization procedures, the fluorescent intensity dropped by only 5% from the first experiment when allyl mercapatan pulsed plasma polymer layers were used as substrate, FIG. 5*a*. In fact the chip could be used 5 times without significant loss of immobilized probes. This was not the case for the commercial slides which exhibited a comparative rapid decrease in performance. A similar result was found for the reusability of the chips with regard denaturing/re-hybridization experiments, FIG. 5*b*.

EXAMPLE 5

Allyl mercaptan was deposited onto polystyrene beads (Biosearch Technologies, Inc.) as described above These thiol functionalised beads were then derivatized with fluorescently tagged DNA strands as described above. The derivatisation was confirmed by fluorescence microscopy, FIG. 6.

The invention claimed is:

1. A method for applying a coating to a substrate, said method including (i) subjecting said substrate to a plasma discharge in the presence of a compound of formula (I) or formula (Ia):

(I)

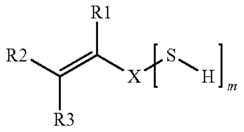

(Ia)

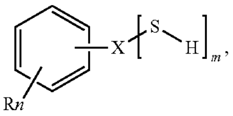

to form a substrate coated with reactive thiol groups, wherein X is an optionally substituted straight or branched alkylene chain(s) or aryl group(s); $R^1$, $R^2$ and $R^3$ are each, independently, hydrogen, optionally substituted hydrocarbyl or heterocyclic groups, and m is an integer greater than 0; $R''$ is a number of optionally substituted hydrocarbyl or heterocyclic groups, where n is 0-5; and (ii) following step (i), reacting at least one of said reactive thiol groups with a thiol-terminated biomolecule to form a disulphide linkage between said substrate and said biomolecule.

2. The method of claim 1, wherein the compound of formula (I) is a compound of formula (II)

(II)

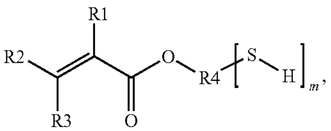

Where R4 is an optionally substituted hydrocarbyl or heterocyclic group.

3. The method of claim 2, wherein the compound of formula (II) is a compound of formula (III)

(III)

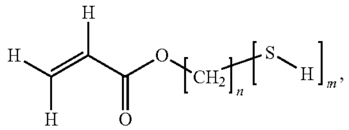

where n=1-20.

4. The method of claim 2, wherein the compound of formula (II) is a compound of formula (IIIa)

(IIIa)

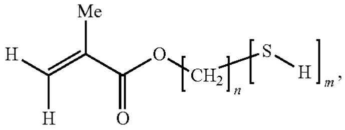

where n=1-20.

5. The method of claim 1, wherein the thiol containing compound of formula (I) is a compound of formula (IV)

(IV)

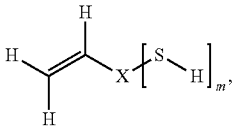

where m=1-20.

6. The method of claim 5, wherein the compound of formula (IV) is a compound of formula (V)

(V)

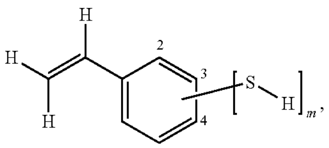

7. The method of claim 5, wherein the compound of formula (IV) is a compound of formula (Va)

(Va)

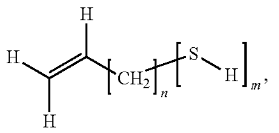

where n=1-20.

8. The method of claim 1, wherein the plasma discharge is pulsed.

9. The method of claim 8, wherein the average power of the pulsed plasma discharge is less than 0.05 $W/cm^3$.

10. The method of claim 8, wherein the pulsed plasma discharge is applied such that the power is on for from 1 μs to 100 μs, and off for from 100 μs to 20000 μs.

11. The method of claim 8, wherein the pulsed plasma discharge is applied such that the pulsing regime changes in a controlled manner throughout the course of a single coating deposition.

12. The method of claim 1, wherein the plasma discharge contains the compound of formula (I) in the absence of any other material.

13. The method of claim 1, wherein additional materials to the compound of formula (I) are added to the plasma discharge.

14. The method of claim 13, wherein said additional materials are inert and are not incorporated within the reactive thiol containing product coating.

15. The method of claim 13, wherein said additional materials are non-inert and possess the capability to modify and/or be incorporated into the reactive thiol containing product coating.

16. The method of claim 15, wherein the use of said non-inert additional materials results in a copolymer coating that contains reactive thiol functionality.

17. The method of claim 1, wherein the introduction of the compound of formula (I) and/or any additional materials into the plasma discharge is pulsed.

18. The method of claim 1, wherein the compound of formula (I) and/or any additional materials are introduced into the plasma discharge in the form of atomised liquid droplets.

19. The method of claim 1, wherein the means for applying the coating is a reel-to-reel equipped plasma deposition apparatus.

20. The method of claim 1, wherein the substrate is subjected to the plasma discharge in a plasma deposition chamber and wherein the plasma deposition chamber is heated.

21. A substrate having a thiol containing coating thereon, obtained by a process according to claim 1.

22. A method for the immobilisation of a thiol-terminated biomolecule at a surface, said method including the application of a reactive thiol containing coating to said surface by a method according to claim 1 to form a reactive thiol containing surface, and then contacting the coating surface with a solution of said thiol-terminated biomolecule under conditions such that the thiol-terminated biomolecule reacts with the reactive thiol containing surface to form a disulphide linkage.

23. The method of claim 22, wherein the immobilisation of the thiol-terminated biomolecule is spatially addressed onto the reactive thiol containing surface, such that said immobilisation occurs only in given spatial locations.

24. The method of claim 23, wherein the thiol-terminated biomolecule is capable of DNA hybridisation.

25. The method of claim 1, wherein the thiol containing coating produced by the method is reacted with a reagent containing noble or precious metals.

26. The method of claim 23, wherein a thiol functionalised polymer coating is applied to specific domains on the substrate surface.

27. The method of claim 1, wherein the substrate is any or any combination of metal, glass, semiconductor, ceramic, polymer, woven or non-woven fibres, natural fibres, cellulosic material or powder.

28. The method of claim 1, wherein $R^1$, $R^2$ and/or $R^3$ include fluoro, chloro, bromo and/or iodo substituents.

29. The method of claim 3, wherein the compound of formula III, where m=1 and n=1, is 2-mercaptoethyl acrylate.

30. The method of claim 4, wherein the compound of formula IIIa, where m=1 and n=1, is 2-mercaptoethyl methacrylate.

31. The method of claim 6, wherein the compound of formula V is 4-mercaptostyrene.

32. The method of claim 7, wherein the compound of formula Va, where m=1 and n=1, is allyl mercaptan.

33. The method of claim 9, wherein the average power of the pulsed plasma discharge is less than 0.0025 $W/cm^3$.

34. The method of claim 25, wherein the noble or precious metals comprise gold or silver.

* * * * *

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Synthetic Construct

<400> SEQUENCE: 1

gcttatcgag ctttc                                                        15


<210> SEQ ID NO 2
<211> LENGTH: 15
<212> TYPE: DNA
<213> ORGANISM: Artificial Sequence
<220> FEATURE:
<223> OTHER INFORMATION: Synthetic Construct

<400> SEQUENCE: 2

gcttatcgag ctttc                                                        15
```

-continued

<210> SEQ ID NO 3
<211> LENGTH: 15
<212> TYPE: DNA
<213> ORGANISM: Artificial Sequence
<220> FEATURE:
<223> OTHER INFORMATION: Syntheitc Construct

<400> SEQUENCE: 3
gaaagctcga taagc 15

<210> SEQ ID NO 4
<211> LENGTH: 15
<212> TYPE: DNA
<213> ORGANISM: Artificial Sequence
<220> FEATURE:
<223> OTHER INFORMATION: Synthetic Construct

<400> SEQUENCE: 4
cgaatagctc gaaag 15